(12) United States Patent  (10) Patent No.: US 9,222,865 B2
Khonsari et al.  (45) Date of Patent: Dec. 29, 2015

(54) FATIGUE ASSESSMENT

(71) Applicants: Michael M. Khonsari, Baton Rouge, LA (US); Mehdi Amiri, College Park, MD (US)

(72) Inventors: Michael M. Khonsari, Baton Rouge, LA (US); Mehdi Amiri, College Park, MD (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 13/974,565

(22) Filed: Aug. 23, 2013

(65) Prior Publication Data

US 2015/0053017 A1 Feb. 26, 2015

(51) Int. Cl.
*G01N 29/14* (2006.01)
*G01N 3/34* (2006.01)
*G01N 3/32* (2006.01)

(52) U.S. Cl.
CPC .. *G01N 3/34* (2013.01); *G01N 3/32* (2013.01); *G01N 2203/0005* (2013.01); *G01N 2203/0073* (2013.01); *G01N 2203/0222* (2013.01); *G01N 2203/0694* (2013.01)

(58) Field of Classification Search
CPC ............ G01N 29/14; G01N 3/32; G01N 3/34
USPC .......................................................... 73/801
See application file for complete search history.

(56) References Cited

U.S. PATENT DOCUMENTS

| 3,934,452 | A | * | 1/1976 | Prevorsek et al. | ............... | 374/47 |
| 4,232,554 | A | * | 11/1980 | Aleck | ............... | 73/577 |
| 8,209,133 | B2 | * | 6/2012 | Darehbidi et al. | ............... | 702/34 |
| 8,285,522 | B1 | * | 10/2012 | Tryon et al. | ....................... | 703/2 |
| 8,965,712 | B2 | * | 2/2015 | Omori et al. | ..................... | 702/34 |
| 2007/0068605 | A1 | * | 3/2007 | Statnikov | ...................... | 148/558 |
| 2009/0000382 | A1 | * | 1/2009 | Sathish et al. | .................. | 73/606 |
| 2009/0048788 | A1 | | 2/2009 | Darehbidi et al. | | |
| 2012/0084019 | A1 | | 4/2012 | Khonsari | | |
| 2015/0226634 | A1 | * | 8/2015 | Matsuura | ....................... | 73/577 |

FOREIGN PATENT DOCUMENTS

WO 2013/105995 7/2013

OTHER PUBLICATIONS

M. Naderi, M. M. Khonsari, Thermodynamic Analysis of Fatigue Failure in a Composite Laminate, J Mechanics of Materials, 2012, pp. 113-122, vol. 46, Elsevier.

* cited by examiner

*Primary Examiner* — Lisa Caputo
*Assistant Examiner* — Octavia Hollington
(74) *Attorney, Agent, or Firm* — John B. Edel; Edel Patents LLC

(57) ABSTRACT

Methods are disclosed relating to the assessment of fatigue damage in objects that include for example, subjecting a fatigued object to a cyclic mechanical stress, measuring a rate of temperature rise in the fatigued object, and assessing a degree of fatigue of the fatigued object based on the rate of temperature rise in the fatigued object. Methods of measuring internal structural characteristics and methods of correlating fatigue damage to results from excitation tests are also taught.

15 Claims, 7 Drawing Sheets

FATIGUE ASSESSMENT

Methods described herein may be used in assessments of pre-existing fatigue in objects. Certain fatigue assessment methods disclosed herein may be used to identify the remaining useful life of an object subject to mechanical fatigue.

A method of evaluating fatigue described herein may, for example, comprise subjecting a fatigued object to a cyclic mechanical stress; measuring a rate of temperature rise in the fatigued object; and assessing a degree of fatigue of the fatigued object based on the rate of temperature rise in the fatigued object. In a related example, the fatigued object may have a substantially uniform temperature prior to the step of subjecting the fatigued object to the cyclic mechanical stress. In a further related example, the cyclic mechanical stress may be selected from shear stress, tensile stress, and compressive stress. In a still further related example, the assessing of the degree of fatigue comprises comparing the rate of temperature rise in the fatigued object to information from a different temperature rise test on a different object and the different object may have a macroscopic structure similar to the fatigued object. In a series of distinct but related examples, the fatigued object may be metallic, plastic, or a composite material. In a further related example, the fatigued object may be heterogeneous. In a still further related example, the rate of temperature rise is measured at the beginning of the subjecting of the fatigued object to the cyclic mechanical stress. In a still further related example, the fatigued object is a rigid object.

A method of measuring internal structural characteristics as described herein may, for example, comprise allowing a fatigued object having a remaining useful life to come to a substantially uniform rest temperature; monitoring the fatigued object with a microstructural damage assessment device; subjecting the fatigued object to a cyclic stress having a duration sufficient to provide a result measurable by the microstructural damage assessment device; measuring the result associated with the cyclic stress; and ceasing the cyclic stress before the cyclic stress causes fatigue sufficient to substantially decrease the remaining useful life of the fatigued object. In a related example, the result may be an increase in the temperature of the fatigued object. In a related example, the result may be an acoustic emission from the fatigued object. In a further related example the microstructural damage assessment device may be a temperature sensing device. In a further related example, the microstructural damage assessment device may be an infrared sensing device. In a still further related example, the duration may be less than 1 minute. In a further related example the cyclic stress may have a cyclic stress amplitude wherein the cyclic stress amplitude is not greater than three times a typical operation stress amplitude.

A method of characterizing useful life may, for example, comprise conducting a first rate of temperature rise test comprising allowing an object to come to a substantially uniform rest temperature, subjecting the object to a cyclic stress sufficient to provide a temperature increase, and taking a first measurement of a first initial rate of temperature rise; repeatedly applying a primary load stress to the object; tracking the application of the primary load stress; conducting a second rate of temperature rise test comprising allowing the object to come to the substantially uniform rest temperature, subjecting the object to the cyclic stress, and taking a second measurement of a second initial rate of temperature rise; and correlating the second measurement with a degree of fatigue. In a related example the primary load stress is applied until the object experiences mechanical failure.

DETAILED DESCRIPTION

Example 1

Figure 1:
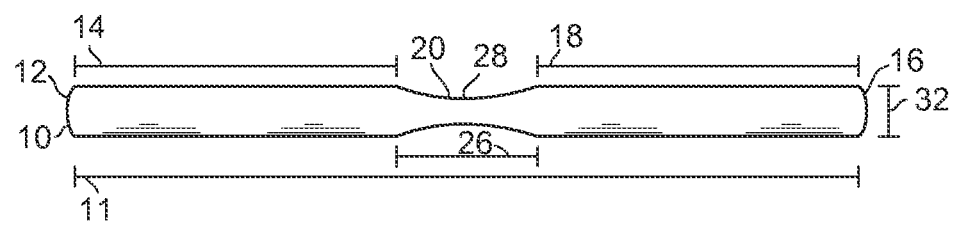
FIG. 1 depicts a stainless steel specimen used in cyclic load testing.

Referring now to FIG. 1 of the drawings, Specimen 10 is a solid 304L stainless steel rod with a tapered center. Specimen 10 has a Specimen width 11 of 215.9 mm with Specimen first section 12 having a Specimen first section width 14 of 88.9 mm, with Specimen second section 16 having a Specimen second section width 18 of 88.9 mm. Tapered region 20 has a Tapered region width 26 of 38.1 mm and a Tapered region minimum diameter 28 of 6.35 mm. Specimen 10 has a Specimen diameter 32 of 12.7 mm. Tapered region 20 has smooth transition past Tapered region minimum diameter 28 such that Tapered region 20 makes out an arc having a radius of 58.67 mm.

Figure 2:
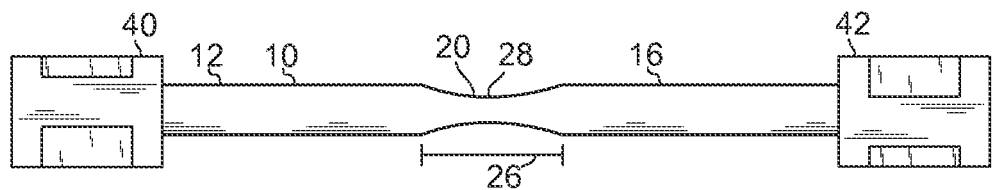
FIG. 2 depicts a stainless steel specimen secured within two collets.

FIG. 2 of the drawings shows Specimen 10 secured within First collet 40 and Second collet 42 as configured for the present example. Specimen first section 12, Specimen second section 16, Tapered region 20, Tapered region width 26, Tapered region minimum diameter 28 as they appear in FIG. 2 are substantially as configured in the description of FIG. 1 above. First collet 40 and Second collet 42 are components of a rotating-bending fatigue apparatus (not shown) which in the present example was the rotating-bending fatigue apparatus model number RBF-300HT produced by Fatigue Dynamics, Inc., 969 Decker Road. Walled Lake, Mich. 48390-3217. The rotating-bending fatigue apparatus was a compact bench-mounted unit with a variable speed motor with a failure cut-off circuit in a control box and a cycle counter. The desired stress level was determined by selecting a percentage of the tensile strength of material and converting that value into a bending moment. As used herein, measurements of stress, σ, can be converted to a bending moment, M, using the following equation wherein M is the bending moment measured in in*lb and σ is the stress measured in megapascal or MPa.

$$M = 0.2225 \left[ \frac{\text{lb} * \text{in}}{\text{MPa}} \right] * \sigma$$

Loads were commonly applied at a frequency of 60 hertz. After the specimen was mounted into First collet 40 and Second collet 42, the speed control was adjusted to bring the machine up to the desired speed and the poise weight of the rotating-bending fatigue apparatus was then positioned and locked into place on the calibrated beam fixing the application of the previously calculated bending moment. Upon fracture of Specimen 10, the machine automatically stopped and the number of cycles to failure was recorded from a cycle counter. The cycle counter was a digital indicator capable of recording up to 99,999,900 cycles.

Properties for the 304L Stainless Steel specimen are indicated in Table 1 which indicates the composition of Specimen 10 and Table 2 which indicates mechanical and thermal properties of Specimen 10. Prior to testing Specimen 10 was polished longitudinally, progressing through 0, 00 and 000 emery paper to remove nicks, dents, scratches and circumferential tool marks from the surface.

TABLE 1

| | Composition, % | | | | | | | | |
|---|---|---|---|---|---|---|---|---|---|
| Material | C | Cr | Fe | Mn | Mo | Ni | P | Si | S |
| SS304L | ≤0.03 | 18.0-20.0 | — | ≤2.0 | — | 8-12 | ≤0.045 | ≤1.0 | ≤0.03 |

Component elements properties of the material.
Note that the numbers with "≤" show the maximum value.

TABLE 2

| Material | Ultimate Strength MPa | Yield Strength MPa | Modulus of Elasticity, GPa | Thermal Conductivity, W/mK |
|---|---|---|---|---|
| SS 304L | 564 | 210 | 193-200 | 16.3 @ 100° C. |

Figure 3:
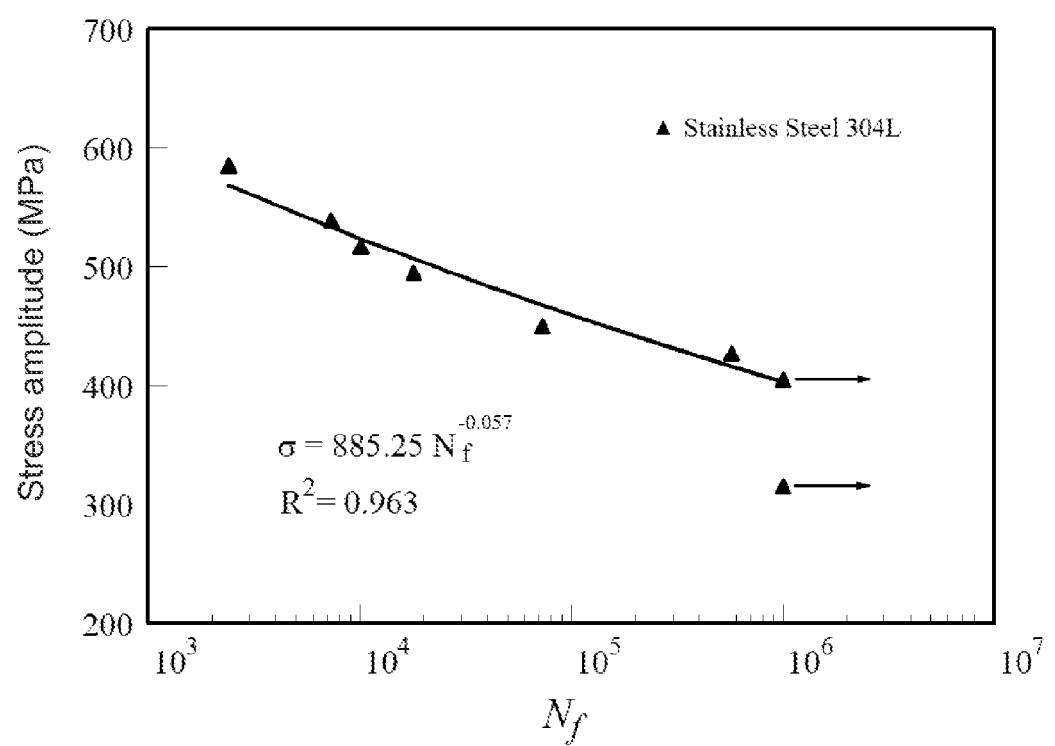
FIG. 3 is a graph showing the relationship between the number of cycles to failure and stress amplitude.

A preliminary series of tests was carried out to characterize the fatigue behavior of the materials. Results were obtained by testing specimens at various loads to provide data for plotting the stress vs. the number of cycles to failure, referred to as the S-N curve. FIG. 3 shows the S-N curve for the Specimens 10 tested at various stress amplitudes. Each of the tests conducted associated with FIG. 3 were performed with a fresh Specimen 10 and run until failure occurred, fracturing Specimen 10 into two pieces Infrared (IR) thermography is used to record the temperature evolution of Specimen 10 during the entire experiment. Temperature measurements for recorded values and used in calculations were average temperature values for the area of specimen 10 experiencing localized temperature rise. The infrared camera used to record Specimen 10 was a model no. M7500 sold under the brand MIKRON available from LumaSense Technologies, Inc. 3301 Leonard Court Santa Clara, Calif. 95054. The infrared camera measure temperature in a range between 0° C. to 500° C., had a resolution of 320×240 pixels, and an accuracy of ±2% of reading, sensitivity/NETD of 0.08° C. at 30° C., and image update rate of 7.5 Hz. Before fatigue testing, the surface of each of the Specimens 10 was sprayed with black paint in order to reduce IR reflections and increase the emissivity of the specimen surface.

Example 2

Using the rotating-bending fatigue apparatus of Example 1 and Specimens 10 that were prepared as described in Example 1 a series of additional tests were conducted. Specimens 10 were subjected to both primary loading and excitation loading. Primary loading was conducted as described in Example 1 with separate tests being conducted on separate Specimens 10 at fatigue loads of 200 MPa, 400 MPa, 450 MPa, 500 MPa, and 550 MPa. Prior to the primary loading test and at intervals during the primary loading test the primary loading was interrupted, Specimen 10 was allowed to cool to room temperature, and an excitation test was conducted. The excitation test was administered using the same configuration as the primary loading test but at a load of 400 MPa. The excitation test was brief, lasting long enough to record specimen temperature over the initial 13 cycles. The temperature of Specimen 10 was recorded by the infrared camera during the excitation test. The initial rate of increase of the temperature during the excitation test was measured for each excitation test. Measurements of the number of cycles to failure of primary loading in the present example were compared to the S-N curve of FIG. 3 to confirm the reliability of the testing procedure of the present example. In the present example, the excitation loading amplitude was not varied and the excitation loading frequency was not varied. The excitation loading amplitude may be different from the fatigue loading amplitude, σ. However, using a consistent excitation loading amplitude allows each result from an excitation loading test to be compared to other results. The excitation test provides information about the current microstructural state and the presence of prior fatigue damage in the specimen.

Figure 4:
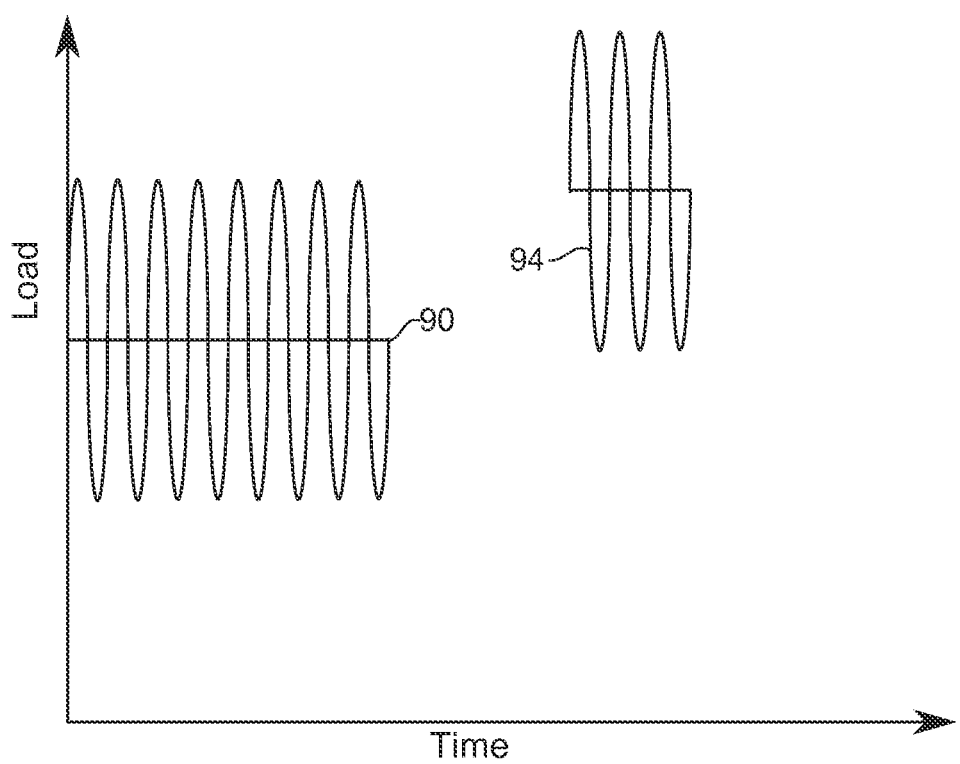
FIG. 4 is a diagram of the transition from primary loading to excitation loading.

FIG. 4 is a diagram of the transition from primary loading to excitation loading. After Primary loading cycle 90 concludes there is a period of time in which Specimen 10 is not loaded and is allowed to cool to room temperature. After Specimen 10 has reached room temperature, Excitation loading cycle 94 begins. Excitation loading cycle 94 does not need to be at the same frequency as Primary loading cycle 90 nor does Excitation loading cycle 94 need to be at the same load amplitude as Primary loading cycle 90. In the present example, the Excitation loading cycle 94 lasted for a short-period of time and was commonly between five and 15 seconds. The short duration of the Excitation loading cycle 94 causes no significant damage to the samples during excitation loading. In the present example the excitation loading amplitude was $\sigma_{exc}$=400 MPa for all tests. Depending on the life duration of the individual Specimens 10, between 5 to 13 excitation tests were performed for each of the Specimens 10. The slope of the temperature, measured at the beginning of each excitation test, may be expressed in the following equation in which $R_\theta$ is the initial slope of the temperature, $N_{acc}$ represents the number of cycles accumulated, f is the loading frequency, and $\sigma_a^m$ is the applied stress amplitude. As used herein initial slope of the temperature rise, $R_\theta$, has the units ° C./s.

$$R_\theta = F(N_{acc}, f)\sigma_a^m$$

The initial slope of the temperature rise at the beginning of the test is intimately related to the accumulated cycles. Five sets of fatigue tests are carried out at primary loading stress amplitudes of σ=200, 400, 450, 500 and 550 MPa to investigate the effect of fatigue loading amplitude on the slope of temperature.

Figure 5:
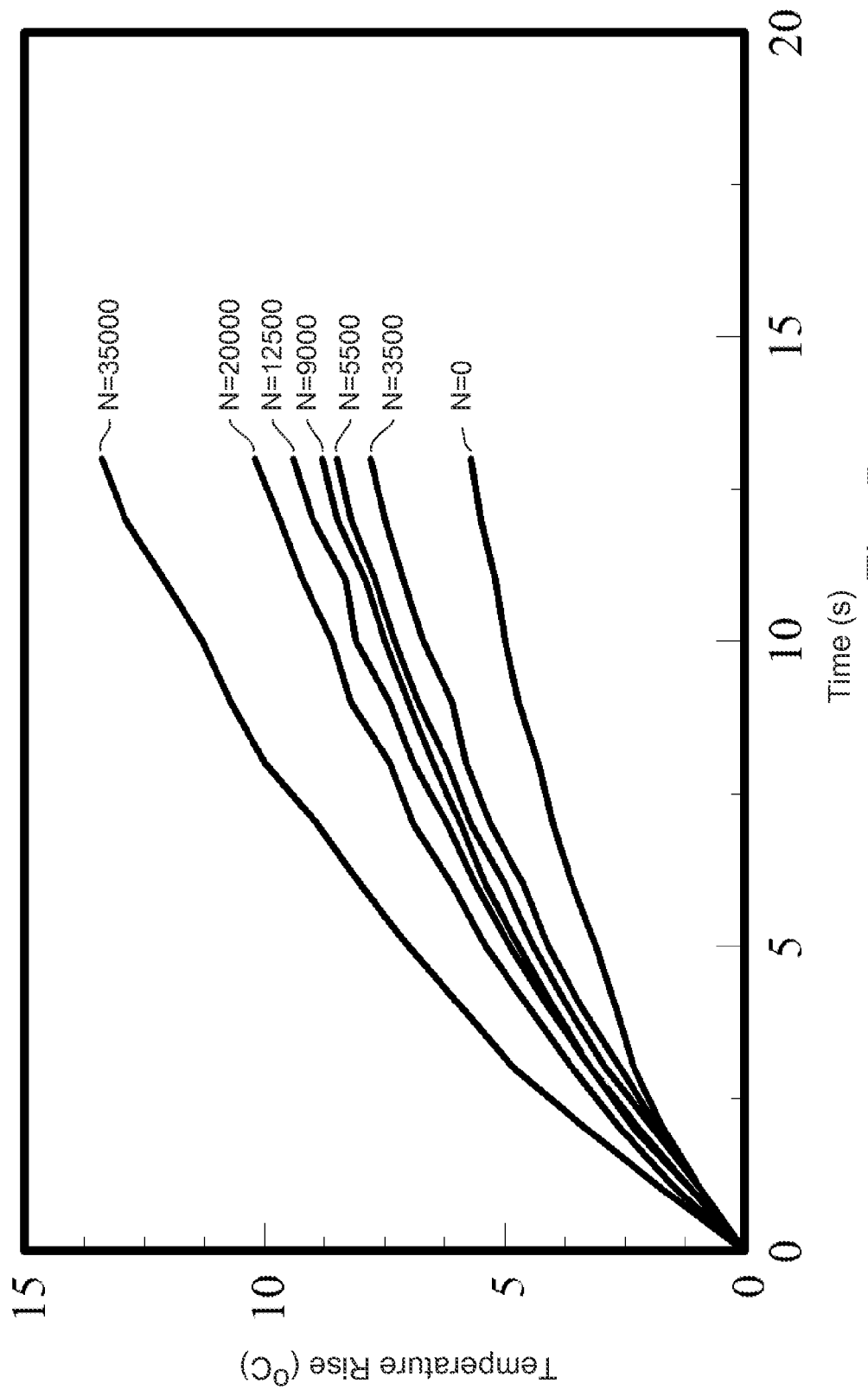
FIG. 5 is a diagram showing temperature rise as a function of the accumulated number of cycles a specimen has undergone.
Figure 6:
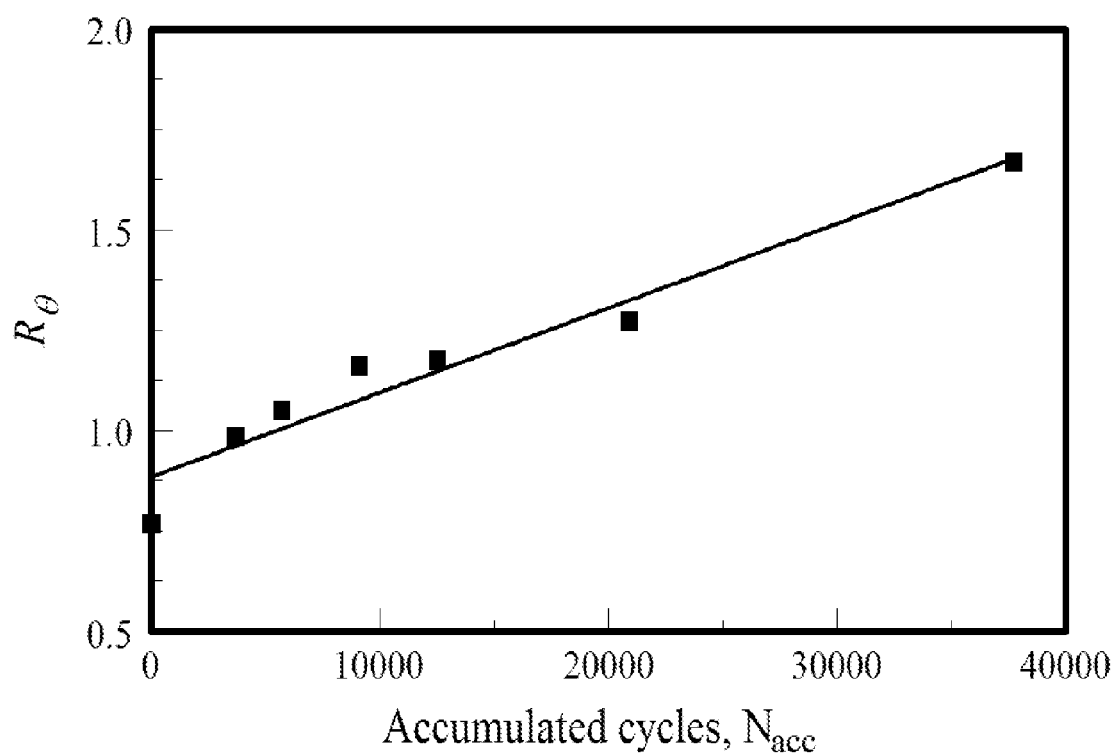
FIG. 6 is a diagram showing the initial rate of temperature rise as a function of the accumulated number of cycles a specimen has undergone.

FIG. 5 shows the temperature rise of a specimen during excitation loading for different accumulated number of cycles. It pertains to the temperature response of a specimen tested at σ=500 MPa for which the fatigue test is stopped at different accumulated number of cycles. For example, N=0 corresponds to the fresh specimen and N=35,000 corresponds to the temperature evolution of the specimen during excitation testing after an accumulation of 35,000 cycles. Tracking the application of the primary load stress by counting the cycles allows for the preparation of accurate correlations between the rate of initial temperature rise and the accumulated fatigue on an object. FIG. 5 shows that as the sample experiences cyclic fatigue, the rate of temperature rise after each stop significantly increases. FIG. 6 shows the initial temperature slope plotted against the number of accumulated cycles. Since the excitation loading amplitude and frequency are kept constant the initial slope of the temperature rise, $R_\theta$, is merely a function of accumulated cycles. $R_\theta$ may therefore be used as a measure of the degradation of Specimen 10. FIG. 6 shows that the initial slope of the temperature rise increases as the accumulated number of cycles increases. An increase in the number of accumulated cycles corresponds to an increase in internal damage.

Figure 7:
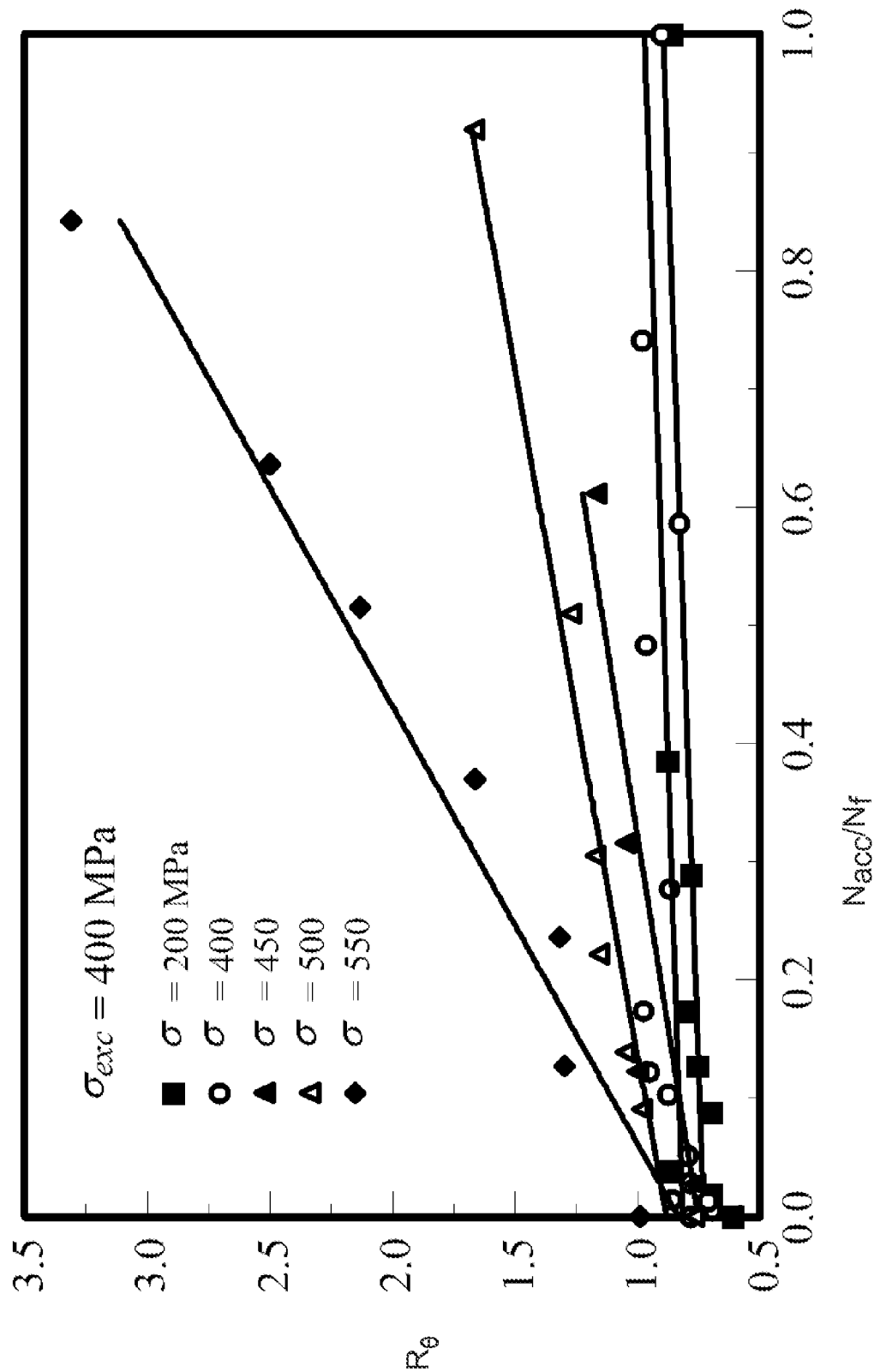
FIG. 7 shows the initial temperature slope data for various stress amplitudes across a normalized range of accumulated cycles.

FIG. 7 shows the initial temperature slope, $R_\theta$, data for the various primary loading stress amplitudes plotted as a function of normalized number of cycles, $N_{acc}/N_f$ where $N_{acc}$ is the accumulated number of cycles and $N_f$ is the number of cycles at failure. It can be seen that there is a linear correlation between the slope and the accumulated cycles. FIG. 7 shows higher stress amplitudes result in greater change in the temperature slope through the life of the specimen. This behavior exhibited in FIG. 7 may be used to predict the remaining fatigue life of a specimen.

Example 3

Figure 8:
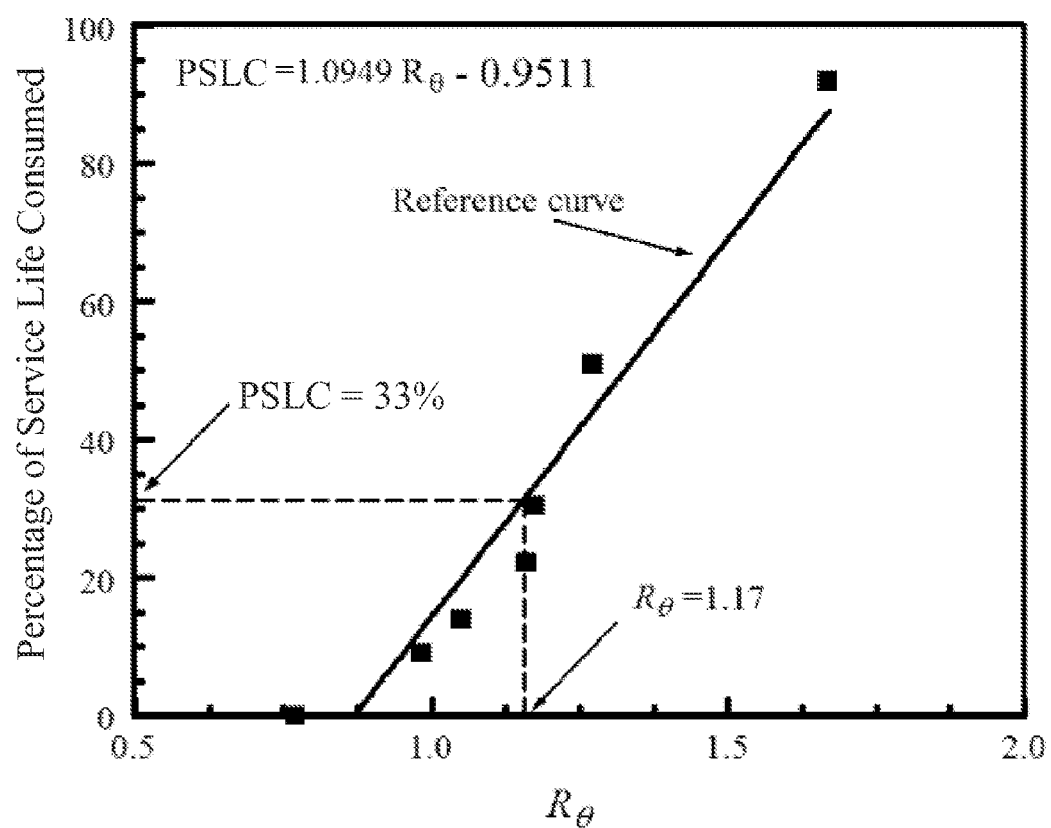
FIG. 8 is a diagram showing the relationship between the percentage of service life consumed and the initial rate of temperature rise from excitation tests.

A separate fatigue test was conducted at a primary loading stress amplitude of 500 MPa to verify the predictive capability of the initial temperature slope measurements. The reference curve for the 500 MPa primary loading stress amplitude is shown in FIG. 8 including a linear curve fit which shows the percentage of the service life consumed (PSLC) plotted against the initial slope of the temperature rise, $R_\theta$. The percentage of service life consumed was calculated as a function of the initial slope of the temperature rise, $R_\theta$ to be:

$$PSLC = 1.0949 R_\theta - 0.9511$$

The fatigue test was stopped at an arbitrary number of cycles to perform the excitation procedure. The results of the excitation test performed using the same procedure described in Example 2 indicated an initial slope of the temperature rise, $R_\theta$ of 1.17° C./s. Comparing the initial slope of the temperature rise to the reference curve of FIG. 8 and the associated curve fit equation it was predicted that the percentage of service life consumed was 33%. The fatigue test was resumed at the primary loading stress amplitude and run until final fracture. The experiment showed that at the time of the excitation test the actual percentage of service life consumed was 31%.

Example 4

The remaining life of a specimen may be predicted according to the following generalized steps. First, an excitation test procedure is developed such that the excitation test produces a type of load on a specimen that is comparable to primary loading. Because the excitation stress amplitude, $\sigma_{exc}$, and the excitation frequency, f, influence the measurement of initial slope of the temperature rise, $R_\theta$, the excitation stress amplitude and the excitation frequency should remain constant for all excitation tests conducted both in the development of a curve fit and for test designed to compare to the curve fit. Second, testing is conducted to develop a reference curve by monitoring the number of cycles throughout a primary loading test run that runs the specimen to failure and periodically subjects the specimen to the excitation tests in which the initial slope of the temperature rise is measured. Data for the initial slope of the temperature rise is plotted against the accumulated number of cycles and that data is curve fit to relate the number of accumulated cycles to the initial slope of the temperature rise. That relationship may be set as a linear relationship. The remaining fatigue life of a sample having experienced an unknown number of primary loading cycles may be predicted in a nondestructive way through short-term mechanical loading in the form of the above established excitation test. The initial slope of the temperature rise for the specimen is then converted into the number of accumulated cycles using the curve fit relationship established in the previous step. Once the estimated number of accumulated cycles is established the number of remaining cycles is simply the difference between the number of accumulated cycles and the number of cycles to failure in the initial testing used to develop the curve fit. The excitation stress amplitude and frequency of the primary loading can be different or the same as the primary loading amplitude and frequency.

Depending on the material, geometry and size of the specimen (structure) the appropriate excitation amplitude and frequency should be selected. Excitation frequency and amplitude may be selected utilizing one or more of the following criteria. The excitation frequency is set such that there is an appreciable rise in the temperature of specimen being tested. The excitation frequency is set high enough that initial temperature rise results may be clearly differentiated from one another for specimens that have undergone different amounts of fatigue. The excitation amplitude is such that plastic deformation of the specimen does not occur during the excitation testing. Further, the excitation frequency, amplitude, and duration are such that the excitation test does not substantially impact the remaining useful life of the object being tested through fatigue.

Examples 1-3 were conducted at ambient temperature in a laboratory. The generalized procedures of the present example may be conducted for load stresses from a wide range of temperatures and other environmental factors. For example, if a specimen normally experiences the load stress at a temperature of 80° C. the testing to develop the reference curve may be conducted at 80° C. to produce a reference curve that is more accurate for the environmental conditions in which the specimen experiences its normal load stress. Other environmental factors potentially impacting the service life of a specimen may similarly be accounted for in testing associated with the preparation of the reference curve.

Example 5

Techniques described herein may be used, for example, to guide replacement decisions for industrial or other equipment. The equipment or a component of the equipment may be tested under a normal operational load or stress to develop a reference curve as described above such that the reference curve describes the relationship of the initial rate of temperature rise for excitation tests to the remaining useful life of the equipment. From the test used to develop the reference curve an initial rate of temperature rise associated with pristine equipment would be known along with the estimated initial rate of temperature rise at or near the time of failure. From those two pieces of information a threshold initial rate of temperature rise may be selected that is in between the initial rate of temperature rise associated with pristine equipment and the initial rate of temperature rise at or near the time of failure. During the operation of the equipment excitation tests may be performed on the equipment to determine whether the initial rate of temperature rise is above the threshold initial rate of temperature rise value. If the initial rate of temperature rise was above the threshold value the equipment would be replaced. Although different reference curves may be associated with primary loads of different amplitudes, the techniques of the present example may be employed as a useful tool for making replacement decisions even when the primary load is not consistent.

Example 6

In a prophetic embodiment, the measurement technique used to establish the initial rate of temperature rise for the excitation tests may be conducted by temperature sensing methods other than infrared thermography. Thermocouples or other direct temperature sensing instruments may be used to detect the surface temperature of a specimen. All such temperature measuring devices including infrared sensing devices may be referred to herein collectively as "temperature sensing devices."

Example 7

The initial rate of temperature rise may be due to a quantity of energy released during the application of a cyclic stress which may be referred to herein as the "excitation energy." Under a properly controlled test, quantification of the excitation energy may be a strong indicator of the remaining life of a fatigued object. In a prophetic embodiment, non-temperature sensing devices may be used to quantify the micro structural damage by quantifying the excitation energy in a manner similar to the assessment techniques that measure the initial rate of temperature rise in a specimen. One example of such a technique is the use of an acoustic emission sensor to quantify the degree of micro structural damage and or excitation energy released in the specimen during an excitation test. In such a technique, an excitation test would be conducted in a manner comparable to the excitation test described above. Data collected from the acoustic emission sensor would then be quantified such that a measure of the excitation energy from the excitation test comparable to the initial rate of temperature rise data could be used to develop a separate reference curve and ultimately used to predict the remaining useful life of specimens. Collectively the temperature sensing devices, acoustic emission sensors and other equipment capable of assessing excitation energy and thus accumulated micro structural damage to a specimen may be characterized as "microstructural damage assessment devices."

In various embodiments described herein and for various contemplated embodiments the type of fatigue experienced by an object during the primary loading is the same general type of fatigue that the object is subjected to for the associated excitation testing. In other words, if the object is subjected to a torquing force as the type of force applied for the primary load, the most appropriate excitation load would be a torquing type load. Similarly if the object is subjected to a tensile stress as the type of force applied for the primary load, the most appropriate excitation load would be a tensile stress load. However, it is not important that the amplitude of the excitation test match the amplitude of the primary stress nor is it important that the frequency of the excitation test match the frequency of the primary stress. The amplitude of the excitation load may be less than three times the amplitude of the primary load.

Although the examples described above relate to rotational fatigue of a metal, the techniques described herein may be used with differing materials and different types of fatigue. For example, tensile fatigue, compression fatigue, and other forms of bending fatigue may each be measured in a similar fashion. The excitation test may be configured to replicate the general type of fatigue that would be considered the primary loading fatigue and may be configured to have a comparable loading frequency and amplitude to the primary loading fatigue. Further, the techniques described herein may be used with a wide variety of materials including various metals, alloys, plastics, composites, glass, ceramic, concrete, wood, and combinations thereof. Specimens may also be solid, hollow, homogeneous or heterogeneous. Among the great number of apparatus that could be tested by methods described herein are pipes, crankshafts, and rotors from various types of equipment including helicopters, jet engines, and power turbines.

As that phrase is used herein a "fatigued object" indicates an object that has undergone substantial micro-structural change associated with fatigue as compared to that same object as it existed in pristine non-fatigued form. An example of a fatigued object would be a driveshaft that has been in service as a driveshaft long enough to have undergone microstructural changes sufficient to alter the useful service life of the driveshaft. As that phrase is used herein, "degree of fatigue" indicates any characterization of an amount of fatigue previously experienced or any characterization of the remaining useful life associated with a fatigued object. For example, an indication of the percentage of useful life remaining in an object would be an assessment of the degree of fatigue of that object.

The above-described embodiments have a number independently useful individual features that have particular utility when used in combination with one another including combinations of features from embodiments described separately. There are, of course, other alternate embodiments which are obvious from the foregoing descriptions of the invention, which are intended to be included within the scope of the invention, as defined by the following claims.

We claim:

1. A method of evaluating fatigue comprising:
   a. subjecting a fatigued object to a cyclic mechanical stress;
   b. measuring a rate of temperature rise in the fatigued object; and
   c. assessing a degree of fatigue of the fatigued object based on the rate of temperature rise in the fatigued object;
   d. wherein the assessing of the degree of fatigue comprises comparing the rate of temperature rise in the fatigued object to information from a different temperature rise test on a different object;
   e. wherein the rate of temperature rise is measured at the beginning of the subjecting of the fatigued object to the cyclic mechanical stress;
   f. wherein the measuring of the rate of temperature rise in the fatigued object occurs during an excitation test;
   g. wherein the fatigued object is an object that has previously undergone substantial micro-structural fatigue changes;
   h. wherein the degree of fatigue assessed is representative of an amount of fatigue experienced prior to the excitation test; and
   i. wherein the amount of fatigue experienced prior to the excitation test is unknown prior to the excitation test.

2. The method of claim 1 wherein the fatigued object has a substantially uniform temperature prior to the step of subjecting the fatigued object to the cyclic mechanical stress.

3. The method of claim 1 wherein the cyclic mechanical stress is selected from shear stress, tensile stress, and compressive stress.

4. The method of claim 1 wherein the different object has a macroscopic structure similar to the fatigued object.

5. The method of claim 1 wherein the fatigued object is metallic.

6. The method of claim 1 wherein the fatigued object is plastic.

7. The method of claim 1 wherein the fatigued object is a composite material.

8. The method of claim 1 wherein the fatigued object is heterogeneous.

9. The method of claim 1 wherein the fatigued object is a rigid object.

10. The method of claim 1 further comprising:
   a. expending a portion of a service life the fatigued object prior to measuring the rate of temperature rise;
   b. wherein the cyclic mechanical stress is part of an excitation test.

11. A method of characterizing useful life comprising:
   a. conducting a first rate of temperature rise test comprising:
      i. allowing an object to come to a substantially uniform rest temperature,
      ii. subjecting the object to a cyclic stress sufficient to provide a temperature increase, and
      iii. taking a first measurement of a first initial rate of temperature rise;
   b. repeatedly applying a primary load stress to the object;
   c. tracking the application of the primary load stress;
   d. conducting a second rate of temperature rise test after the repeated application of the primary load stress, with the second rate of temperature rise test comprising:
      i. allowing the object to come to the substantially uniform rest temperature,
      ii. subjecting the object to the cyclic stress, and
      iii. taking a second measurement of a second initial rate of temperature rise; and
   e. correlating the second measurement with a degree of fatigue;
   f. wherein the second measurement of the second initial rate of temperature rise occurs during an excitation test and
   g. wherein the object is an object that has undergone substantial micro-structural fatigue changes during the application of the primary load stress to the object.

12. The method of claim 11 further comprising the step of continuing subjecting the object to the primary load stress until the object experiences mechanical failure.

13. A method of evaluating fatigue comprising:
   a. subjecting a first object to a first load stress until the first object fails;
   b. performing a series of excitation tests on the first object wherein the series of excitation tests is carried out over a life of the first object;
   c. preparing a set of initial slope of temperature rise data from the series of excitation tests;
   d. subjecting a second object to a second load stress sufficient to fatigue the second object;
   e. subjecting the second object to a subsequent excitation test
   f. determining a subsequent initial slope of temperature rise in the second object during the subsequent excitation test; and
   g. evaluating a degree of fatigue of the second object based on the subsequent initial slope of temperature rise in the second object during the subsequent excitation test and the set of initial slope of temperature rise data from the series of excitation tests;
   h. wherein the first object has a first object macroscopic structure;
   i. wherein the second object has a second object macroscopic structure; and
   j. wherein the first object macroscopic structure is similar to the second object macroscopic structure prior to failure of the first object.

14. The method of claim 13 further comprising the step of indicating a percentage of the service life consumed for the second object.

15. The method of claim 13 further comprising the step of expressing the degree of fatigue as a function of the subsequent initial slope of temperature rise.

* * * * *